(12) United States Patent
Lin et al.

(10) Patent No.: US 6,864,370 B1
(45) Date of Patent: Mar. 8, 2005

(54) PROCESS FOR MANUFACTURING OXYCODONE

(76) Inventors: Zhaiwei Lin, 301 Skylane Dr., Apt. A3, Plymouth, IN (US) 46563; Charles Auxilium Francis, 2205-2 La Porte Ave., Valparaiso, IN (US) 46383; Christopher Arne Kaldahl, 400 Hiawatha Ave., Apt. 311, LaPorte, IN (US) 46350; Kazimierz Grzegorz Antczak, 545 S. Shore Dr., Culver, IN (US) 46511; Vijai Kumar, 67 Whitewood Dr., Morris Plains, NJ (US) 07950

( * ) Notice: Subject to any disclaimer, the term of this patent is extended or adjusted under 35 U.S.C. 154(b) by 3 days.

(21) Appl. No.: 10/455,202

(22) Filed: Jun. 5, 2003

(51) Int. Cl.[7] .................. C07D 515/08; C07D 515/06
(52) U.S. Cl. ........................... 546/44; 546/45
(58) Field of Search ..................... 546/44, 45

(56) References Cited

U.S. PATENT DOCUMENTS

| | | | |
|---|---|---|---|
| 4,045,440 A | * | 8/1977 | Rapoport et al. ............. 546/44 |
| 4,472,253 A | * | 9/1984 | Schwartz ............... 204/157.71 |
| 4,795,813 A | * | 1/1989 | Schwartz .................... 546/45 |
| 5,112,975 A | * | 5/1992 | Wallace ...................... 546/45 |
| 6,008,355 A | | 12/1999 | Huang et al. ................ 546/45 |
| 6,090,943 A | * | 7/2000 | Mudryk et al. .............. 546/44 |
| 6,177,567 B1 | | 1/2001 | Chiu et al. ................... 546/47 |

FOREIGN PATENT DOCUMENTS

| | | | |
|---|---|---|---|
| EP | 0 943 617 A1 | 9/1999 | ......... C07D/489/02 |

OTHER PUBLICATIONS

*Helvetica Chimica Acta*, vol. 60 (1977), pp. 2135–2137.
*Arch. Pharm. Pharm. Med. Chem.*, (1996), pp. 325–326.
*Heterocycles*, vol. 49 (1998), pp. 43–47.
*Journal of the Chemical Society*, Oct. 1960, pp. 4139–4140.
*Journal of Medicinal Chemistry*, vol. 17 (1974), 1117.

* cited by examiner

*Primary Examiner*—Rita Desai

(57) ABSTRACT

Oxycodone is manufactured in high yields and with a high purity using codeine or a salt of codeine as the starting material. The manufacturing process involves the following steps:

(a) codeine or a codeine salt (e.g., codeine phosphate) is converted into the intermediate N-carboalkoxy- or N-carboaryloxynorcodeine,
(b) the intermediate N-carboalkoxy- or N-carboaryloxynorcodeine resulting from step (a) is oxidized to yield the intermediate N-carboalkoxy- or N-carboaryloxynorcodeinone;
(c) the intermediate N-carboalkoxy- or N-carboaryloxynorcodeinone resulting from step (b) is enolized with a base and the resultant enolate is thereafter methylated to yield the intermediate N-carboalkoxy- or N-carboaryloxynorthebaine;
(d) the intermediate N-carboalkoxy- or N-carboaryloxynorthebaine resulting from step (c) is reduce to yield thebaine;
(e) the thebaine resulting from step (d) is oxidized to yield the intermediate 14-hydroxycodeinone; and
(f) the intermediate 14-hydroxycodeinone resulting from step (e) is hydrogenated to yield oxycodone.

18 Claims, No Drawings

US 6,864,370 B1

PROCESS FOR MANUFACTURING OXYCODONE

FIELD OF THE INVENTION

Oxycodone is manufactured in high yields and in a highly pure form by a multistep manufacturing process that utilizes codeine or a codeine salt as the starting material.

BACKGROUND OF THE INVENTION

Oxycodone is a well know narcotic employed for pain management. Page 1245 of the thirteenth edition of the Merck Index states that oxycodone may be prepared " . . . by catalytic reduction of hydroxycodeinone, its oxime, or its bromination products or by reduction of hydoxycodeinone with sodium hydrosulfite."

The prior art describes several methods for oxycodone using codeine or a salt thereof as the starting material. Codeine along with morphine, thebaine and oripavine may be extracted from poppy straw—see U.S. Pat. No. 6,067,749 issued May 30, 2000 to Fist et al Codeine is also readily prepared by the methylation of morphine, which is present in poppy straw in a higher percentage than that of codeine.

U.S. Pat. No. 6,177,567 B1 issued Jun. 23, 2001 to Chiu et al. discloses a method for the preparation of oxycodone and salts thereof which involves the oxidation of codeine to codeinone, formation of a dienolsilyl ether congener of codeinone in strong amine base, oxidation of the dienolsilyl ether congener using peracetic acid and hydrogenation of the 14-hydroxycodeinone product.

In an article by Ivor Brown and M. Martin-Smith appearing on pp. 4139–4140 of the *Journal of The Chemical Society* (October, 1960), the authors disclose several methods for the oxidation of codeine to 14-hydroxycodeinone (which may then be reduced to oxycodone) involving the use of oxidants such as manganese dioxide or chromic oxide in acetic acid.

U.S. Pat. No. 6,008,355 issued Dec. 28, 1999 to Huang et al. discloses two methods for preparing oxycodone from codeine. The first method involves oxidizing codeine so as to form codeinone and thereafter converting the codeinone to oxycodone in a two-step, one-pot reaction involving the reaction of codeinone with hydrogen peroxide in water in the presence of an acid at about 15 to about 70° C. to form 14-hydroxycodeinone and then catalytically hydrogenating 14-hydroxycodeinone in its original reaction mixture to form oxycodone.

The second method disclosed in the '355 patent involves oxidizing codeine so as to form codeinone, reacting codeinone with an acylating agent in water or a solubilizing solvent mixture in the presence of an acid at about 15 to about 70° C. to form acyldienolate, oxidizing the dienolate to 14-hydroxycodeinone and then catalytically hydrogenating 14-hydroxycodeinone in its original reaction mixture to form oxycodone.

All of the prior art methods for preparing oxycodone from codeine or a salt thereof are disadvantageous from a commercial manufacturing point of view in several respects: The purity of the oxycodone is relatively low, thereby requiring considerable additional costly purification steps (and attendant loss of yield) to raise the purity to an acceptable level. A second disadvantage of prior art methods is that they require the use of expensive reagents and the reactions are very time-consuming and are quite sensitive to reaction conditions. Thirdly, and most importantly, the prior art methods result in poor yields or the oxycodone and therefore such methods are unsuitable for commercial manufacturing operations.

OBJECT OF THE INVENTION

It is the principal object of this invention to prepare oxycodone with a high level of purity and sufficiently high yields so as to result in a commercially feasible manufacturing operation.

DETAILED DESCRIPTION OF THE INVENTION

The process of the invention for the manufacture of oxycodone comprises the following steps:

(a) converting codeine or a codeine salt into the intermediate N-carboalkoxy- or N-carboaryloxynorcodeine;

(b) oxidizing the intermediate N-carboalkoxy- or N-carboaryloxynorcodeine to yield the intermediate N-carboalkoxy- or N-carboaryloxynorcodeinone, (c) enolizing the intermediate N-carboalkoxy- or N-carboaryloxynorcodeinone with a base and methylating the resultant enolate to yield the intermediate N-carboalkoxy- or N-carboaryloxynorthebaine;

(d) reducing the intermediate N-carboalkoxy- or N-carboaryloxynorthebaine to yield thebaine;

(e) oxidizing the thebaine to yield the intermediate 14-hydroxycodeinone; and (f) hydrogenating the intermediate 14-hydroxycodeinone to yield oxycodone Step (a) may be carried out by reacting the codeine or a codeine salt, e.g., codeine phosphate, with a chloroformate in the presence of an alkali metal carbonate or alkali metal bicarbonate and an inert solvent. Preferably, the chloroformate is a methyl, ethyl or phenylchloroformate. The alkali metal is typically sodium or potassium. Suitable examples of the inert solvent that may be used in step (a) include methylene chloride, chloroform, 1,2-dichloroethane and the like. Typically, the selected chloroformate will be utilized in an amount of about 1.5 to about 8.0 moles per mole of codeine or codeine salt. In general, the inert solvent will be present in the amount of about 10 to about 60, preferably 20 to 25, liters per kilogram of codeine or the selected codeine salt. The reaction involved in step (a) may be carried out at a temperature of about 0 to about 85° C., preferably 42–70° C., e.g., when the selected inert solvent is chloroform, the reaction is typically carried out under reflux at 65° C. The reaction time will typically be in the range of about 10 to about 72 hours, preferably 10 to 24 hours. The reaction in step (a) proceeds smoothly and completion of the reaction may be determined by high-pressure quid chromatography.

Preferably, the intermediate N-carboalkoxy- or N-carboaryloxynorcodeine is not isolated, and step (b) is carried out in the same reaction vessel as employed for step (a).

Step (b) may be carried out by oxidizing the intermediate N-carboalkoxy- or N-carboaryloxynorcodeine with a suitable oxidizing agent in the presence of an inert solvent (which may be the same inert solvent as employed in step (a)). Suitable oxidizing agents include aluminum alkoxide and a ketone; a potassium alkoxide and a ketone; dimethyl sulfoxide in the presence of oxalyl chloride; manganese dioxide; potassium dichromate in the presence of sulfuric acid; and air in the presence of palladium (II) acetate. The preferred oxidizing agent comprises manganese dioxide. In general, the oxidizing agent will be used in an amount of about 7 to about 9 moles per mole of N-carboalkoxy- or N-carboaryloxynorcodeine.

Useful inert solvents for carrying out step (b) include chlorinated hydrocarbons such as chloroform, methylene chloride 1,2-dichloroethane and the like; hydrocarbons such as benzene or toluene; esters such as ethyl acetate; and ethers such as tetrahydrofuran. The preferred solvents are chloroform and toluene. In general, the inert solvent will be utilized in an amount of about 10 to about 50, preferably 20 to 25, liters per kg of the intermediate resulting from step (a).

The oxidation reaction of step (b) may be carried out at temperatures of about 0 to about 60° C., preferably 20–25° C. Typically, the oxidation reaction for step (b) will entail a reaction time of about 6 to about 49, preferably 18 to 24, hours.

Preferably, the intermediate N-carboalkoxy- or N-carboaryloxynorcodeinone produced in step (b) is not isolated, and step (c) is carded out in the same reaction vessel as employed for step (b).

In step (c), the intermediate N-carboalkoxy- or N-carboaryloxynorcodeinone produced in step (b) is enolized using a base in an inert solvent and the resultant dienolate salt is thereafter methylated using a methylating agent. Suitable bases for carrying out the enolization reaction include sodium hydride, sodium t-butoxide, potassium t-butoxide and lithium diisopropylamide. Suitable inert solvents for carrying out the enolization reaction (and the subsequent methylation reaction) include tefrahydrofuran, N-methylpyrrolidinone, dimethylformamide, toluene, dimethyl ether, methyl t-butyl ether, dioxane and the like.

The preferred solvent for carrying out both the enolization and the methylation reactions in step (c) comprises a mixture of about 1 part to about 20, preferably 4 parts, of tetrahydrofuran per part of N-methylpyrrolidinone. In general, the inert solvent employed in step (c) is employed in an amount of about 10 to about 50, preferably 20 to 30, liters per kg of the intermediate N-carboalkoxy- or N-carboaryloxynorcodeinone produced in step (b).

The methylation reaction may be carried out with typical methylating agents such as dimethyl sulfate, dimethyl carbonate, methyl iodide, methyl bromide, diazomethane and the like. In general, the methylating agent will be employed in an amount of about 2 to about 4 moles per mole of N-carboalkoxy- or N-carboaryloxynorcodeine.

The enolization reaction as well as the subsequent methylation reaction involved in step (c) are typically conducted at temperatures in the range of about −20 to about 50° C., preferably −5 to 5° C. The typical reaction time for cab out both the enolization reaction as well as the methylation reaction involved in step (c) will be about 2 to about 24, preferably 8 to 15, hours.

Preferably, the intermediate N-carboalkoxy- or N-carboaryloxynorthebaine produced in step (c) is not isolated, and step (d) is carried out in the same reaction vessel as employed for step (c).

In step (d), the intermediate N-carboalkoxy- or N-carboaryloxynorthebaine is reduced to yield the intermediate thebaine. The reducing agent preferably comprises lithium aluminum hydride or sodium bis(2-methoxyethoxy) aluminum hydride (borane-tetrahyrofuran complex or borane-dimethyl sulfide complex may also be used). The reaction is generally carried out in an inert solvent such as tetrahydrofuran (which is preferred), dimethyl ether, diethyl ether, methyl t-butyl ether, and the like. Typically, such inert solvent will be utilized in an amount of 10 to about 50, preferably 20 to 30, liters per kg of the intermediate N-carboalkoxy- or N-carboaryloxynorthebaine produced in step (c).

In general, the reducing agent will be employed in step (d) in an amount of about 1 to about 3 moles per mole of N-carboalkoxy- or N-carboaryloxynorthebaine. Typically, step (d) is carried out a temperature of about 0 to about 60° C., preferably 20 to 25° C. The reaction time for carrying out the reduction reaction involved in step (d) will be about 1 to about 20, preferably 8–12, hours.

Preferably, the intermediate thebaine produced in step (d) is isolated as an acid addition salt. The isolation of the thebaine as an acid addition salt preferably involves the reaction of the tbebaine with L-tartaric acid in a $C_1$–$C_4$ alcohol acetone or a mixture thereof with water. In general, the isolation of the thebaine entails the use of about 1 to about 1.5 moles of L-tartaric acid per mole of thebaine produced in step (d). Typically, the $C_1$–$C_4$ alcohol, acetone or a mixture thereof with water will be utilized in an amount of about 5 to about 20, preferably 10–15, parts of such solvent per part of thebaine produced in step (d). If a mixture of the $C_1$–$C_4$ alcohol or acetone with water is utilized as the solvent, the water may be present in an amount of about 5 parts to about 20 parts per 100 parts of die $C_1$–$C_4$ alcohol or acetone. The preferred solvent is a mixture of methanol and water. The isolated thebaine bitartrate addition salt is recovered in a very high yield with a very high level of purity as a result of this isolation technique.

The thebaine is preferably utilized in the form of its bitartrate addition salt as the starting material for step (e). If desire the thebaine tartrate addition salt may be converted to the thebaine free base (e.g., by reaction with a slight excess of a dilute aqueous base such as sodium hydroxide) and such free base may be used as the starting material for step (e).

In step (e), the intermediate thebaine (in the form of its bitartrate addition salt or in the form of its free base) is oxidized to 14-hydroxycodeinone. For step (e), the oxidizing agent preferably comprises hydrogen peroxide, peracetic acid; m-chloroperbenzoic acid; singlet oxygen; oxone or iodosylbenzene. In general, the oxidizing agent will be utilized in an amount of about 1 to about 1.5 moles per mole of thebaine or thebaine bitartrate.

Typically, the oxidation reaction of step (e) is conducted in the presence of a solvent such as formic acid, acetic acid, a $C_1$–$C_4$ alcohol, water and mixtures thereof. A preferred solvent for use in carrying out the oxidation reaction comprises about 2 to about 15, preferrably 5 to 10, parts per part of thebaine or thebaine bitartrate, of a mixture of formic acid, water and isopropanol in a ratio of about 1.5:1:1.

The oxidation reaction of step (e) occurs in two stages within an overall temperature range of about −20 to about 70° C., preferably 0 to 45° C. The first stage of the reaction is carried out at a cold temperature and the second stage of the reaction is carried out at a higher temperature. The reaction time for step (e) is typically in the range of about 2 to about 16, preferably 2 to 6, hours Preferably, the intermediate 14-hydroxycodeinone produced in step (e) is not isolated, and step (f) is carried out in the same reaction vessel as employed for step (e).

Step (f) involves the hydrogenation of the intermediate 14-hydroxycodeinone produced in step (e) to the final product oxzycodone. The hydrogenation catalyst may be Raney nickel a noble metal (e.g., palladium on carbon), an oxide of a noble metal, sodium hydrosulfite and the like. The hydrogenation will be carried out at a pressure of about 15 to about 60 psi, and the hydrogation catalyst will be utilized in an amount of about 0.001 to about 0.015 mole per mole of the 14-hydroxycodeinone. The hydrogenation reaction is typically carried out in a solvent that may be any of the same solvents and in the same amounts as indicated above for carrying out step (e).

The hydrogenation reaction involved in step (f) may take place in a temperature of about 0 to about 50° C., preferably 20 to 25° C. The typical reaction time for step (f) is in the range of about 2 to about 36, preferably 16 to 26, hours.

At the completion of step (f), the oxycodone may be isolated as a free base or a suitable acid addition salt.

The following nonlimiting examples shall serve to illustrate the preferred embodiments of the present invention. Unless otherwise indicated to the contrary, amounts and percentages are on a weight basis.

Example 1

Preparation of N-Carboethoxynorcodeine

A 500 ml round-bottomed flask is charged with 20 g of codeine phosphate hemi-hydrate, 120 ml of chloroform, 60 ml of water and 17 ml of concentrated (28–30%) aqueous ammonia. The mixture is stirred for a minimum of 20 minutes the stirring is stopped and the layers are allowed to separate. The bottom organic layer is separated, washed with 25 ml of water and diluted with an additional 170 ml of chloroform.

The chloroform solution is heated to reflux and dried azeotropically until no water separation is observed (3 to 5 hours). After cooling to room temperature, 8.5 g of fine anhydrous potassium carbonate is added and the reaction mixture is heated to reflux. With vigorous stirring while under refux, a solution of 13.5 g of ethylchloroformate in 85 ml of chloroform is added to the reaction mixture over a period of 1 to 2 hours. Thereafter, the reaction mixture is stirred while under reflux until the reaction is complete, typically 6 to 12 hours.

With stirring, approximately 300 ml of solvent is distilled off under reduced pressure (e.g., 50 mm Hg). Thereafter, 330 ml of toluene is added, with stirring, to the reaction mixture and the distillation is continued until all of the chloroform has been replaced by the toluene. The reaction mixture is cooled to room temperature. The inorganic salts are filtered off and the filter cake is washed with 30 to 50 ml of toluene. The volume of the filtrate is then adjusted to a total of 305 ml with additional anhydrous toluene. The filtrate contains 16.4 g (93% yield) of the intermediate N-carboethoxynorcodeine having a purity of greater than 95% as measured by HPLC. The intermediate is an oil and the toluene solution is used in step (b) (i.e., Example 2) without purification.

Example 2

Preparation of N-Carboethoxynorcodeinone

Manganese dioxide is added at the rate of about 8 g/hour, with vigorous stirring, to the toluene solution of the N-carboethoxynorcodeine obtained in Example 1. Typically, a total of 32–34 g of manganese dioxide is required to complete the oxidation reaction involved in step (b) of the process of the invention. The reaction time for the oxidation reaction is typically 6 to 12 hours. The manganese dioxide is filtered off and the filter cake is washed with three 40 ml portions of toluene. The filtrates are combined and the toluene solution is distilled under reduced pressure (e.g., 50 mm Hg) until the final volume has reached 34 ml. Thereafter, 180 ml of tetrahydrofuran is added to the residue. The tetrahydrofuran solution contains 15.5 g (95% yield) of N-carboethoxynorcodeinone having a typical purity of greater than 93% as measured by HPLC. The product is an oil and is used in step (c) (i.e., Example 3) without purification.

Example 3

Preparation of N-Carboethoxynorthebaine

Into a 500 ml round-bottomed flask is charged 14.7 g of potassium t-butoxide, 60 ml of N-methylpyrrolidinone and 60 ml of tetrahydrofuran. The mixture is stirred at room temperature for a minimum of 30 minutes and is then cooled to a temperature of 0 to 5° C. The solution obtained from Example 2 is slowly added, with stirring, while maintaining the temperature below 5° C. The reaction mixture is allowed to warm up to room temperature and is stirred at room temperature for 2 hours. The solution is then cooled to a temperature of 0 to 5° C. Thereafter, while stirring and maintaining the temperature below 5° C., 15.5 g of dimethyl sulfate is slowly added. The reaction mixture is then warmed up to room temperature and stirred at room temperature for a minimum of two hours. 60 ml of water is then added with stirring and the reaction mixture is then distilled at reduced pressure (e.g., 50 mm Hg) until the volume has reached approximately 110 ml 60 ml of water is then added with stirring to the residue and the mixture is then extracted with two 180 ml portions of toluene. The toluene portions are combined and then washed with 15 ml of water. The solution is then dried azeotropically by heating to reflux and the toluene is distilled off until the volume of the residue is approximately 30 ml. Thereafter, 85 ml of anhydrous tetrahydrofuran is added. The tetrahydrofuran solution contains 13.7 g (85% yield) of N-carboethoxynorthebaine having a purity level of greater than 90% as measured by HPLC. The product is an oil and is used in step (d) of the process of the invention (i.e., Example 4) without purification.

Example 4

Preparation of Thebaine Bitartrate Monohydrate

Into a 500 ml round-bottomed flask is charged 1.85 g of lithium aluminum hydride and 85 ml of anhydrous tetrahydrofuran. The suspension is vigorously stirred and the tetrahydrofuran solution of N-carboethoxynorthebaine prepared in Example 3 is slowly added. The reaction is exothermic and during the addition, the temperature is maintained below 40° C.

After completion of the addition of the tetrahydrofuran solution of N-carboethoxynorthebaine, the reaction mixture is stirred at room temperature for 4 to 6 hours. Thereafter, 2.3 g of water, 2.3 g of a 15% aqueous solution of sodium hydroxide followed by 5.5 g of water are slowly added. The reaction mixture is then stirred at room temperature for 1 to 2 hours. The solids are filtered off and the filter cake is washed with three 15 ml portions of tetrahydrofuran. The tetrahydrofuran is distilled off under reduced pressure (e.g., 50 mm Hg) and is replaced with methanol, which is added in sufficient quantity to adjust the volume of the reaction mixture to 120 ml.

To the reaction mixture under reflux is added 7.1 g of L-tartaric acid in 10 ml of water. The suspension is cooled and is stirred at 0 to 5° C. for 2 to 3 hours. The solids are filtered off and the filter cake is washed with two 15 ml portions of cold methanol. After drying in vacuo (e.g., 50 mm Hg) at a temperature of 30 to 40° C., 14.5 g (82% yield) of thebaine bitartrate monohydrate is obtained. The purity level of the thebaine bitartrate monohydrate is greater than 99% as measured by HPLC. The total yield of thebaine bitartrate monohydrate based on the starting material, i.e., codeine phosphate hemi-hydrate, is 61.5%.

Example 5

Preparation of 14-Hydroxycodone

A 250 ml round-bottomed flask is charged with 14.5 g of the thebaine bitartrate monohydrate prepared in Example 4, 29 ml of water, 29 ml of isopropanol and 43 ml of formic acid. With stirring, the reaction mixture is cooled to 0–5° C. and 3.4 ml of 30% hydrogen peroxide are added. The mixture is stirred at 0–5° C. for 1–2 hours and thereafter is heated to 40 to 45° C. and is stirred at this temperature for 2–3 hours. The resultant solution containing 8.58 g (90% yield) of 14-hydroxycodeinone is cooled and is used in step (f) (i.e., Example 6) of the process of the invention without purification.

Example 6

Preparation of Oxycodone

To the solution of 14-hydroxycodeinone produced in Example 5 is added 0.5 g of 5% palladium on carbon, 50% wet. The mixture is hydrogenated at 30 to 40 psi for a period of 18 to 25 hours at ambient temperature. The catalyst is filtered off and is washed with 5 ml of water. The filtrate is cooled to 0–5° C. and with stirring, sufficient concentrated (28–30%) ammonium hydroxide is added to raise the pH to 10–12. The resulting suspension is stirred at 0–5° C. for 1–2 hours. The solid is filtered off and is washed with two 5 ml portions of water. The product is dried in vacuo (e.g., 50 mm Hg) at 30–40° C. to yield 8.1 g of oxodone (85% yield based on thebaine bitartrate). The product purity is better than 98%.

Example 7

Preparation of Oxycodone Hydrochloride 8.1 g of oxycodone obtained in Example 6 and 80 ml of ethanol are placed in a 250 ml round-bottomed flask. The mixture is heated to reflux. Into the hot mixture is added 10 ml of a concenrated solution of hydrogen chloride in isopropanol. The mixture is cooled and stirred at 0–5° C. for 1–2 hours. The product is filtered off and the filter cake is washed with a small amount of cold ethanol. After drying in vacuo (e.g., 50 mm Hg) at 30–40° C., 77 g (85% yield) of pure oxycodone hydrochloride is obtained.

What is claimed is:

1. A process for manufacturing oxycodone, which comprises the steps of:
   (a) converting codeine or a codeine salt into the intermediate N-carboalkoxy- or N-carboaryloxynorcodeine;
   (b) oxidizing the intermediate N-carboalkoxy- or N-carboaryloxynorcodeine to yield the intermediate N-carboalkoxy- or N-carboaryloxynorcodeinone;
   (c) enolizing the intermediate N-carboalkoxy- or N-carboaryloxynorcodeinone with a base and methylating the resultant enolate to yield the intermediate N-carboalkoxy- or N-carboaryloxynorthebaine;
   (d) reducing the intermediate N-carboalkoxy- or N-carboaryloxynorthebaine to yield thebaine;
   (e) oxidizing the thebaine to yield the intermediate 14-hydroxycodeinone; and
   (f) hydrogenating the intermediate 14-hydroxycodeinone to yield oxycodone.

2. The process of claim 1 wherein step (a) is carried out by reacting the cods or a codeine salt with a chloroformate in the presence of an alkali metal carbonate or alkali metal bicarbonate and an inert solvent.

3. The process of claim 2 wherein the alkali metal carbonate comprises potassium carbonate and the chloroformate is selected from the group consisting of methyl, ethyl and phenyl chloroformate.

4. The process of claim 2 wherein the inert solvent employed in step (a) is selected from the group consisting of methylene chloride, chloroform and 1,2-dichlorethane.

5. The process of claim 1 wherein step (b) is carried out by using an oxidizing agent selected from the group consisting of an aluminum alkoxide and a ketone; a potassium alkoxide and a ketone; dimethyl sulfoxide in the presence of oxalyl chloride; manganese dioxide; potassium dichromate in the presence of sulfuric acid; and air in the presence of palladium (II) acetate.

6. The process of claim 5 wherein the oxidizing at comprises manganese dioxide.

7. The process of claim 1 wherein step (c) is carried out using a base in an inert solvent and the resultant dienolate salt is thereafter methylated using a methylating agent.

8. The process of claim 7 wherein the base employed in step (c) is selected from the group consisting of sodium hydride, sodium t-butoxide, potassium t-butoxide and lithium diisopropylamide.

9. The process of claim 7 wherein the inert solvent employed in step (c) comprises N-methylpyrrolidinone, a mixture of tetrahydrofuran and N-methyl-pyrrolidinone or a mixture of toluene and N-methylpyrrolidinone.

10. The process of claim 7 wherein the methylating agent is selected from the group consisting of dimethyl sulfate, dimethyl carbonate, methyl iodide, methyl bromide and diazomethane.

11. The process of claim 1 wherein step (d) is carried out using a reducing agent selected from the group consisting of lithium aluminum hydride, sodium bis(2-methoxyethoxy) aluminum hydride, borane-tetrahydrofuran complex and borane-dimethyl sulfide complex.

12. The process of claim 1 further comprising isolating the thebaine in step (d) in the form of an acid addition salt.

13. The process of claim 12 wherein the thebaine is isolated in the form of its bitartrate salt by reacting the thebaine with L-tartaric acid in the presence of a solvent selected from the group consisting of a $C_1$–$C_4$ alcohol, acetone and mixtures thereof with water.

14. The process of claim 13 wherein the thebaine is utilized in the form of its bitartrate salt as the starting material for step (e).

15. The process of claim 1 wherein the thebaine in step (d) is manufactured without isolating or purifying any of the intermediates produced in the course of steps (a)–(c).

16. The process of claim 1 wherein step (e) is carried out by using an oxidizing agent selected from the group consisting of hydrogen peroxide; peracetic acid; m-chloroperbenzoic acid; singlet oxygen; oxone and iodosylbenzene.

17. The process of claim 1 wherein step (f) is carried out using a hydrogenation catalyst selected from the group consisting of Raney nickel; a noble metal; an oxide of a noble metal and sodium hydrosulfite.

18. The process of claim 1 wherein at the completion of step (f), the oxycodone is isolated in the form of its hydrochloride salt.

* * * * *